United States Patent [19]

Tschopp et al.

[11] Patent Number: 4,895,800
[45] Date of Patent: Jan. 23, 1990

[54] YEAST PRODUCTION OF HEPATITIS B SURFACE ANTIGEN

[75] Inventors: Juerg F. Tschopp; Michael M. Harpold; James M. Cregg; Richard G. Buckholz, all of San Diego, Calif.

[73] Assignee: Phillips Petroleum Company, Bartlesville, Okla.

[21] Appl. No.: 801,713

[22] Filed: Nov. 26, 1985

[51] Int. Cl.[4] ...................... C12P 21/00; C12P 21/02; C12N 15/00; C12N 5/00
[52] U.S. Cl. ................. 435/69.3; 435/172.3; 435/255; 435/256; 435/320; 935/28; 935/37; 935/56; 935/65; 935/69; 536/27
[58] Field of Search ............... 435/68, 91, 172.3, 255, 435/320, 256, 254, 938; 935/28, 37, 56, 65, 69; 536/27

[56] References Cited

U.S. PATENT DOCUMENTS

| | | | |
|---|---|---|---|
| 4,320,194 | 3/1982 | Bull | 435/7 |
| 4,428,941 | 1/1984 | Galibert et al. | 424/177 |
| 4,510,245 | 4/1985 | Cousens et al. | 435/172.3 |
| 4,515,714 | 5/1985 | Kawahara | 260/112 |
| 4,769,238 | 9/1988 | Rutter et al. | 424/89 |
| 4,803,164 | 2/1989 | Hitzman et al. | 435/68 |

FOREIGN PATENT DOCUMENTS

| | | |
|---|---|---|
| 73657 | of 0000 | European Pat. Off. . |
| 105149 | 4/1984 | European Pat. Off. . |
| 106828 | 4/1984 | European Pat. Off. . |
| 120551 | 10/1984 | European Pat. Off. . |
| 135435 | 3/1985 | European Pat. Off. . |
| 138704 | 4/1985 | European Pat. Off. . |

OTHER PUBLICATIONS

Miyanohara et al., *Proc. Natl. Acad. Sci.*, vol. 80, pp. 1–5, "Expression of hepatitis B surface antigen gene in yeast".

Hitzeman et al., *Nucl. Acids Res.*, vol. 11, pp. 2745–2763, "Expression of hepatitis B virus surface antigen in yeast".

Couderc et al., *Biol. Abst.*, vol. 71, No. 62361, 1980, "Oxidation of methanol by the yeast Pichia postoris strain IF P-206 purification and properties of the alcohol oxidase".

Scherer et al., *Proc. Natl. Acad. Sci.*, vol. 76(10), Oct. 1979, pp. 4951–4955, "Replacement of chromosome segments with altered DNA sequences constructed in vitro".

Roggenkamp et al., *Mol. Gen. Conf.* vol. 174, pp. 489–493, May 2, 1984, "Biosynthesis and regulation of the pentisonal methanol oxidase from the methylotropic yeast *Hansenula polymorph*".

Ledoboer et al., *Nucl. Acids Res.*, vol. 13(9) May 10, 1985, pp. 3063–3082, "Molecular cloning and characterization of a gene coding for methanol oxidase from *Hansenula polymorph*".

Janowicz et al., *Nucl. Acids Res.*, vol. 139(9) May 10, 1985, pp. 3043–3062, "Cloning and characterization of the DHAS gene encoding the major methanol assimilating enzyme".

Nature, P. Valenzuela et al, vol. 280, pp. 815–819 (8/30/79).

Proc. Natl. Acad. Sci. U.S.A., P. MacKay et al, vol. 78 (7), pp. 4510–4514 (7/81).

DNA, C. Liu et al, vol. 1 (3), pp. 213–221 (1982).

Nature, P. Valenzuela et al, vol. 298, pp. 347–350 (9/82).

Nucleic Acids Research, Y. Ono et al, vol. 11 (6), pp. 1747–1757 (1983).

Proc. Natl. Acad. Sci. U.S.A., D. Wampler et al, vol. 82, pp. 6830–6834 (10/85).

*Primary Examiner*—Robin Teskin
*Attorney, Agent, or Firm*—Hal Brent Woodrow; J. E. Phillips

[57] ABSTRACT

Novel DNA constructs comprising regulatory regions plus the structural coding region for hepatitis B surface antigen (HBsAg) are disclosed. The regulatory regions employed are responsive to methanol, non-catabolite repressing carbon sources and catabolite repressing carbon sources followed by carbon source starvation. The novel constructs are incorporated into a variety of linear and circular plasmids. Such plasmids are used to transform suitable hosts and ultimately used for the production and isolation of hepatitis B surface antigen in high yields.

31 Claims, 11 Drawing Sheets

YEAST PRODUCTION OF HEPATITIS B SURFACE ANTIGEN

This invention relates to the use of recombinant DNA technology for the production of hepatitis B surface antigen. In one aspect, the present invention relates to the production of hepatitis B surface antigen in yeast. In another aspect, the present invention relates to the production of hepatitis B surface antigen in yeast. In another aspect, the present invention relates to novel DNA constructs encoding hepatitis B surfaces antigen. In yet another aspect, the present invention relates to novel organisms transformed with the above described DNA constructs.

Background

As recombinant DNA technology has developed in recent years, the controlled production by microorganisms of an enormous variety of useful polypeptides has become possible. Many eukaryotic polypeptides, such as for example, human growth hormone, leukocyte interferons, human insulin and human proinsulin have already been produced by microorganisms. The continued application of techniques already in hand in expected in the future to permit production by microorganisms of a variety of other useful polypeptide products. One such useful polypeptide product is hepitatis B surface antigen.

Hepatitis B (serum hepatitis) virus is transmitted among humans and manifests itself as chronically debilitating infections which can result progressively in severe liver damage, primary carcinoma, and, ultimately, death. In most cases, complete recovery from hepatitis B infections can be expected. However, large segments of the population, especially in many African and Asian countries, are chronic carriers with the dangerous potential of transmitting the disease pandemically.

Effective prophylaxis of the hepatitis B virus is to administer a hepatitis B virus vaccine which is usually a highly purified hepatitis B surface antigen. Such a hepatitis B virus vaccine is effective for preventing infection with the virus. Especially high risk groups are those people who need blood transfusions or dialysis treatment, medical personnel working with such groups, and the like. In addition, such vaccine is also effective for preventing generation of new carrier, and it may therefore be possible to eliminate completely the hepatitis B virus from earth.

The hepatitis B virus has not been infections in cell culture and can, therefore, only be obtained from infected humans or higher primates. Thus, means have not been available for obtaining and maintaining sufficient supplies of hepatitis B virus for use in producing antigen for immunization against hepatitis B virus.

The hepatitis B virus vaccine is usually prepared by isolating and purifying hepatitis B surface antigen from blood plasma of hepatitis B virus carriers. Such purification, however, must be done extremely efficiently since only very low concentrations of the desired antigen are present in the plasma being purified. Hence, it has heretofore been very difficult to prepare the desired hepatitis B virus vaccine on an industrial scale.

OBJECTS OF THE INVENTION

An object of the invention, therefore, is a method for the production of hepatitis B surface antigen in high yields.

Another object of the present invention is the preparation of novel DNA constructs which are capable of expressing hepatitis B surface antigen in high levels.

These and other objects of the invention will become apparent from the disclosure and claims herein provided.

STATEMENT OF THE INVENTION

In accordance with the present invention, it has been discovered that hepatitis B surface antigen can be produced in high yields by culturing yeast cells transformed with DNA constructs comprising hepatitis B surface antigen coding sequences under the control of regulatory regions which are responsive to methanol, non-catabolite repressing carbon sources and carbon source starvation.

The following abbreviations are used in the Figures to represent the restriction enzymes employed.

| Abbreviation | Restriction Enzyme |
|---|---|
| As | AsuII |
| B | BamHI |
| $B_2$ | BglII |
| Bc | BclI |
| C | ClaI |
| $H_2$ | HincII |
| $H_3$ | HindIII |
| K | KpnII |
| $Nd_1$ | NdeI |
| Nr | NruI |
| Ps | PstI |
| $Pv_1$ | PvuI |
| $Pv_2$ | PvuII |
| $R_1$ | EcoRI |
| $R_5$ | EcoRV |
| S | SalI |
| Sp | SphI |
| Ss | SstI |
| St | StuI |
| Xb | XbaI |
| Xh | XhoI |

In the attached figures, restriction sites employed for manipulation of DNA fragments, but which are destroyed upon ligation, are indicated by enclosing the abbreviation for the destroyed site in parenthesis.

DETAILED DESCRIPTION OF THE INVENTION

In accordance with the present invention, there is provided a novel DNA fragment comprising a regulatory region and a polypeptide coding region wherein the polypeptide coding region codes for hepatitis B surface antigen or portions thereof and the regulatory region is capable of controlling the transcription of messenger RNA when positioned at the 5'-end of the polypeptide-encoding gene. The combination of regulatory region, hepatitis B surface antigen (HBsAg) gene, and a transcriptional terminator fragment is referred to hereinafter as an expression cassette or expression unit. The regulatory region employed in the practice of the present invention is responsive to at least one of the conditions selected from the group consisting of:

the presence of methanol in the culture medium with which a host organism containing the expression cassette is in contact, the presence of a non-catabolite repressing carbon source other than methanol in the culture medium with which a host organism containing the expression cassette is in contact, and carbon source starvation in the culture medium with which a host organism containing the expression cassette is in contact after the host organism has been grown on a catabolite- repressing carbon and energy source.

Further in accordance with the present invention, there are provided novel linear and circular plasmids containing the above described expression cassettes.

Still further in accordance with the present invention, there are provided essentially pure cultures of yeast strains transformed with the above described linear or circular plasmids.

In accordance with another embodiment of the present invention, process for preparing hepatitis B surface antigen is described which comprises cultivating a yeast strain transformed with the above described plasmids under conditions where expression of the desired protein product is obtained.

The regulatory regions employed in the practice of the present invention are characterized by their ability to respond to media containing:

(1) methanol, (2) non-catabolite repressing carbon sources such as, for example, glycerol, galactose, acetate and the like, (3) catabolite repressing carbon sources, such as, for example, glucose, ethanol, fructose and the like, followed by carbon source starvation.

Figure 1:
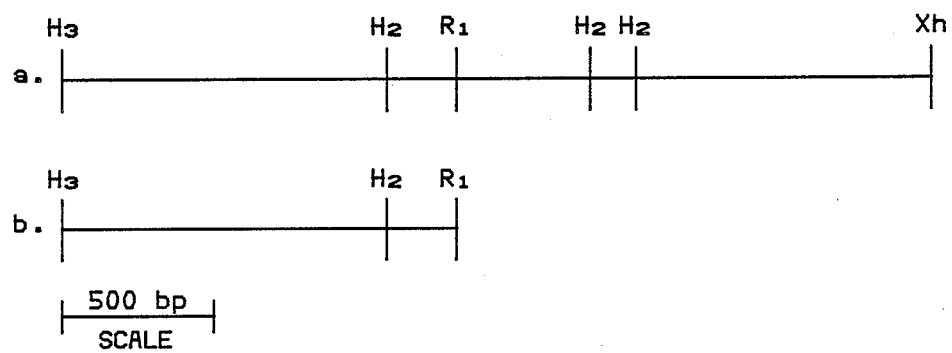
FIG. 1 is a restriction map of the Pichia dihydroxyacetone synthase gene (DAS) regulatory region.
Figure 2:
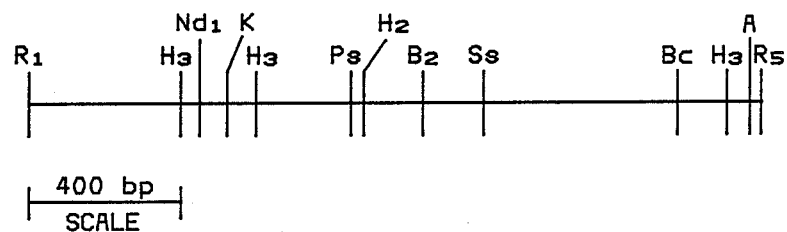
FIG. 2 is a restriction map of the primary Pichia alcohol oxidase gene (AOX1) regulatory region.
Figure 3:
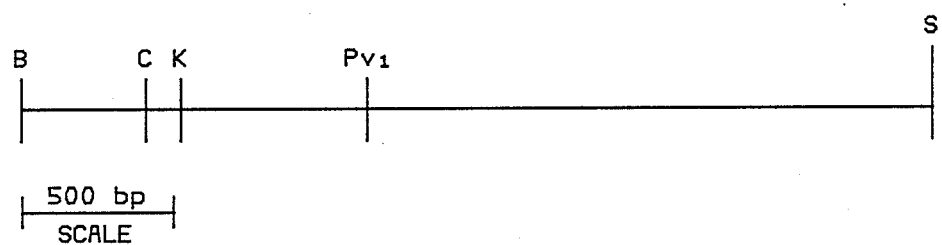
FIG. 3 is a restriction map of the Pichia p40 gene regulatory region.
Figure 4:
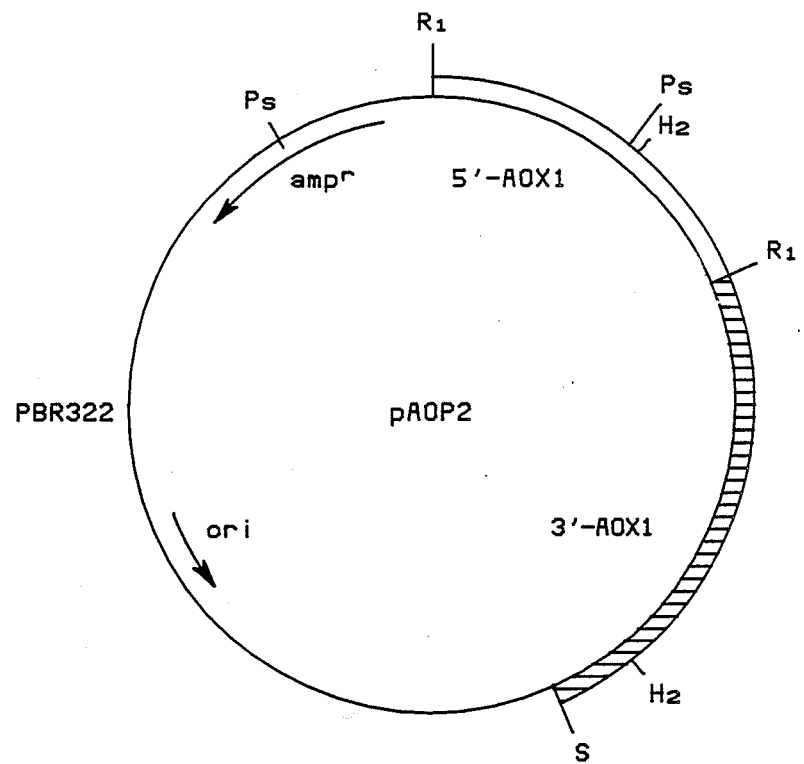
FIG. 4 is a restriction map of plasmid pAOP2.

Exemplary regulatory regions which satisfy the above criteria are depicted by the restriction maps set forth in FIGS. 1, 2 and 3. The regulatory region depicted in FIG. 1 is derived from the dihydroxyacetone synthase (DAS) gene of Pichia pastoris. The regulatory region depicted in FIG. 2 is derived from the primary alcohol oxidase (AOX1) gene of Pichia pastoris (Pichia has two alcohol oxidase genes, referred to herein as AOX1 and AOX2). The regulatory region depicted in FIG. 3 is derived from the p40 gene of Pichia pastoris. Those of skill in the art recognize that other regulatory regions having the above described properties can be isolated from methylotrophic yeasts, such as for example, Pichia pastoris. Such additional regulatory regions having regulatory properties similar to the properties of the above described regulatory regions are also within contemplation of the present invention.

The hepatitis B surface antigen (HBsAg) gene has been previously isolated (Valenzuela et al. (1979) Nature 280, 815) and is available by appropriate restriction enzyme treatment of a variety of vectors, such as for example, pHBS-5 (see FIG. 6, and Valenzuela et al. (1982), Nature 298, 347), pHBV-T-1A (Genetech, EPA 73,657), pHBS-56 (ATCC accession No. 40,047; see EPA 120,551), etc.

The hepatitis B surface antigen gene was modified by Bal31 exonuclease treatment to remove viral noncoding sequences at the 5'-end of the hepatitis gene. The 3'-end of the HBsAg gene was modified by endonuclease digestion and addition of a linker to remove viral noncoding sequences at the 3'-end of the hepatitis gene. The hepatitis B surface antigen gene was further modified to incorporate convenient restriction sites for the manipulation of the DNA fragment. The resulting DNA fragment is an EcoRI-StuI insert, and has the following nucleotide sequence:

```
5'-GAATTCATGG  AGAACATCAC  ATCAGGATTC  CTAGGACCCC
   TGCTCGTGTT  ACAGGCGGGG  TTTTTCTTGT  TGACAAGAAT
   CCTCACAATA  CCGCAGAGTC  TAGACTCGTG  GTGGACTTCT
   CTCAATTTTC  TAGGGGGATC  TCCCGTGTGT  CTTGGCCAAA
   ATTCGCAGTC  CCCAACCTCC  AATCACTCAC  CAACCTCCTG
   TCCTCCAATT  TGTCCTGGTT  ATCGCTGGAT  GTGTCTGCGG
   CGTTTTATCA  TATTCCTCTT  CATCCTGCTG  CTATGCCTCA
   TCTTCTTATT  GGTTCTTCTG  GATTATCAAG  GTATGTTGCC
   CGTTTGTCCT  CTAATTCCAG  GATCAACAAC  AACCAGTACG
   GGACCATGCA  AAACCTGCAC  GACTCCTGCT  CAAGGCAACT
   CTATGTTTCC  CTCATGTTGC  TGTACAAAAC  CTACGGATGG
   AAATTGCACC  TGTATTCCCA  TCCCATCGTC  CTGGGCTTTC
   GCAAAATACC  TATGGGAGTG  GGCCTCAGTC  CGTTTCTCTT
   GGCTCAGTTT  ACTAGTGCCA  TTTGTTCAGT  GGTTCGTAGG
   GCTTTCCCCC  ACTGTTTGGC  TTTCAGCTAT  ATGGATGATG
   TGGTATTGGG  GGCCAAGTCT  GTACAGCATC  GTGAGTCCCT
   TTATACCGCT  GTTACCAATT  TTCTTTTGTC  TCTGGGTATA
   CATTTAAGGC  CT-3'
```

The regulatory region-structural gene constructs of the present invention can be supplied to organisms for amplification, reproduction and expression in a variety of ways. For autonomous replication in yeast, an autonomous replication sequence (ARS) element is useful. Examples include PARS1 and PARS2 derived from Pichia pastoris (See copending U.S. application Ser. No. 666,577, Cregg inventor and assigned to Phillips Petroleum Co.). Where integrative transformation of the host is instead desired, no ARS element will be employed. A preferred method to achieve integrative transformation has been described in copending application Ser. No. 791,013, by Cregg, assigned to Phillips Petroleum Co., and involves employing a site directed integration vector which comprises a first insertable DNA fragment,
a selectable marker gene, and
a second insertable DNA fragment.

The first and second insertable DNA fragments are each at least about 200 nucleotides in length and have nucleotide sequences which are homologous to portions of the genomic DNA of species of the genus Pichia. The various components of the integrative vector are serially arranged forming a linear fragment of DNA such that the expression cassette and the selectable marker gene are positioned between the 3' end of the first insertable DNA fragment and the 5' end of the second insertable DNA fragment. The first and second insertable DNA fragments are oriented with respect to one another in the serially arranged linear fragment as they are so oriented in the genome of Pichia.

It is necessary to include at least one selectable marker gene in the DNA used to transform the host strain. This facilitates selection and isolation of those organisms which have incorporated the transforming DNA. The marker gene confers a phenotypic trait to the transformed organism which the host did not have, e.g., restoration of the ability to produce a specific amino acid where the untransformed host strain has a defect in the specific amino acid biosynthetic pathway.

Those of skill in the art recognize that additional DNA sequences can also be incorporated into the vectors employed in the practice of the present invention, such as for example, bacterial plasmid DNA, bacteriophage DNA, and the like. Such sequences enable the amplification and maintenance of these vectors in bacterial hosts.

Expression in Transformed Yeast

The above-described plasmids of the present invention have utility in yeast strains which can be transformed. Regulation of gene expression in yeast by the novel DNA fragments of the present invention can be accomplished by subjecting the transformed organisms to carbon source starvation. Carbon source starvation after growth on a variety of both catabolite repressing and non-catabolite repressing carbon sources induces expression of the gene product maintained under the control of the regulatory regions of the invention. Another means to achieve expression of the desired gene product in appropriate species of transformed yeast is to grow transformed yeasts on methanol. Yet another means to induce expression of the desired gene product is to grow transformed yeast on media containing non-catabolite repressing carbon sources.

The regulatory regions of this invention are useful for expression in all yeast strains, since the regulatory regions have been shown to be induced under a variety of conditions. Thus, yeasts capable of growth on methanol or on non-catabolite repressing carbon sources can be caused to produce foreign, i.e., heterologous, polypeptides directly; while yeasts capable of growth on catabolite repressing carbon sources can be caused to produce foreign polypeptides by subjected yeast cells so grown to conditions of carbon source starvation.

Transformed yeast strains which are preferred in the process of the present invention include members of the genera: Candida, Kloeckera, Saccharomyces, Schizosaccharomyces, Rhodotorula, Hansenula, Torulopsis, Pichia, and Kluyveromyces.

Yeasts from these genera are preferred because their safety of handling, growth conditions and the like have been established and are well known to those of skill in the art.

Especially preferred yeast strains for use in one embodiment of the process of the present invention are those yeast strains which are capable of growth on methanol as carbon and energy source. Yeasts known to be capable of growth on methanol include members of the genera: Candida, Kloeckera, Saccharomyces, Rhodotorula, Hansenula, Torulopsis, and Pichia.

Since the regulatory regions of the present invention are also induced by growth on non-catabolite repressing carbon sources as well as conditions of carbon source starvation, yeast strains which are capable of growth on such non-methanolic substrates as: glucose, acetate, glycerol, ethanol, lactose, galactose, fructose, sucrose, and the like and mixtures of any two or more thereof are also useful in the practice of the invention. By growing the host organism on a suitable non-catabolite repressable, non-methanolic carbon source such as, for example, glycerol or galactose, or by growing the host organism on a suitable catabolite repressable carbon source such as, for example, ethanol, glucose and fructose, then subjecting the host organism to carbon source starvation conditions, expression of a gene product under the control of the regulatory regions of the invention can be achieved.

An especially preferred host yeast strain is the mutant *Pichia pastoris* GS115, which is a mutant defective in the ability to produce histidine. GS115 has been designated as having the mutant genotype his4, as a result of the defect in the histidine pathway affecting the histinol dehydrogenase-encoding gene. GS115 is derived from *Pichia pastoria* NRRL Y-11430 and has been deposited with the Northern Regional Research Center of the United States Department of Agriculture in Peoria, Illinois, and has been assigned the accession number NRRL Y-15851. This particular host is useful because it is an auxotrophic mutant deficient in the histidine pathway. Transformation of this host with a vector containing, among other DNA sequences, sequences encoding the HIS4 gene function, allows ready selection of transformed hosts.

Another preferred yeast strain for use in the practice of the present invention is the mutant *Pichia pastoris* GS190, which is a mutant defective in the arginine pathway affecting the arginosuccinate lyase encoding gene. GS190 is derived from Pichia pastoris NRRL Y-11430, and has been deposited with the Northern Regional Research Center of the U.S. Department of Agriculture in Peoria, Ill., and has been assigned the accession number NRRL Y-18014.

Yet another preferred host yeast strain is the double auxotrophic mutant PPF1, which is a mutant defective in both the histidine and arginine pathways. PPF1 is defective in both the histidine pathway affecting the histidinol dehydrogenase encoding gene and the arginine pathway affecting the argininosuccinate lyase encoding gene.

PPF1 has been deposited with the Northern Regional Research Center of the U.S. Department of Agriculture in Peoria, Ill., and has been assigned the accession number NRRL Y-18017.

*Escherichia coli* is also a suitable host for the plasmids of the invention. Those of skill in the art recognize that many strains of *E. coli* are suitable hosts. Several strains employed in the present work are summarized below:

| Strain designation | Accession Number |
|---|---|
| MC1061 | None known |
| LE392 | ATCC #33572 |
| MM294 | ATCC #33625 |

*Pichia pastoris* Transformation Procedure

The experimental procedures for the transformation of *Pichia pastoris* have been previously described, and are presented in greater detail below (Example I).

*Pichia pastoria* can be transformed by enzymatic digestion of the cell walls to give spheroplasts; the spheroplasts are then mixed with the transforming DNA and incubated in the presence of calcium ions and polyethylene glycol, then regenerated in selective growth medium deficient in histidine. The transforming DNA includes the HIS4 gene in which the host strain is deficient, thus only transformed cells survive on the selective growth medium employed.

Hepatitis B Surface Antigen Extraction

Those of skill in the art are aware of numerous methods available for the extraction of a heterologous protein from a unicellular recombinant host. Any of the techniques known by those of skill in the art for cell disruption and protein concentration and/or extraction from the disrupted cells are suitable for recovery of the HBsAg produced in accordance with the present invention.

Hepatitis B Surface Antigen Assays

The transformed cells were grown under appropriate conditions for expression, as described above. Then, following cell breakage, the soluble and insoluble fractions were analyzed for HBsAg. The soluble fraction was analyzed from 22 nm particle with a commercially available "AUSRIA ® II" analysis kit (Abbott Laboratories). Both the soluble and insoluble fractions were analyzed for monomer by employing Western blotting procedures which used antisera raised against the monomeric form of HBsAg and radioactive $^{125}$I-labeled protein A.

The invention will now be described in greater detail with reference to the following non-limiting examples.

EXAMPLES

The following abbreviations are used throughout the examples, with the following meaning:

| | |
|---|---|
| SDS | sodium dodecylsulfate |
| EDTA | ethylenediamine tetraacetic acid |
| TEMED | N,N,N',N'-tetramethylenediamine |
| DTT | dithiothreitol |
| BSA | bovine serum albumin |
| EtBr | ethidium bromide |
| PMSF | phenylmethylsulfonyl fluoride |
| Ci | Curie |
| Zymolyase 60,000 | Source: Miles Laboratories |

The buffers and solutions employed in the following examples have the compositions give below:

| | |
|---|---|
| 1M Tris buffer | 121.1 g Tris base in 800 mL of $H_2O$; adjust pH to the desired value by adding concentrated (35%) aqueous HCl; allow solution to cool to room temperature before final pH adjustment, dilute to a final volume of 1L. |
| TE buffer | 1.0 mM EDTA in 0.01 M (pH 7.4) Tris buffer |
| PBS (Phosphate buffered saline) | 10 mM sodium phosphate (pH 7.0) 0.15 M NaCl |
| SDS Gel Loading Buffer | 62.5 mM Tris-HCl (pH 6.8) 2% SDS 10% glycerol 100 mM dithiothreitol 0.001% bromphenol blue |
| YPD Medium | 1% Bacto-yeast extract 2% Bacto-peptone 2% Dextrose |
| SD Medium | 6.75 g yeast nitrogen base without amino acids (DIFCO) 2% Dextrose in 1 L of water |
| SED | 1 M Sorbitol 25 mM EDTA 50 mM DTT |
| SCE Buffer | 9.1 g Sorbitol 1.47 g Sodium citrate 0.168 g EDTA 50 mL $H_2O$ —pH to 5.8 with HCl |
| CaS | 1 M Sorbitol 10 mM $CaCl_2$ —filter sterilize |
| PEG Solution | 20% polyethylene glycol-3350 10mM $CaCl_2$ 10mM Tris-HCl (pH 7.4) —filter sterilize |
| SOS | 1 M Sorbitol 0.3 × YPD medium 10 mM $CaCl_2$ |

Basal Salt Composition (for fermentor growth of transformed Pichia

| Basal Salts | per liter | |
|---|---|---|
| $H_3PO_4$, 85% | 4.2 | mL |
| $CaSO_4.2H_2O$ | 0.18 | gm |
| $K_2SO_4$ | 2.86 | gm |
| $MgSO_4.7H_2O$ | 2.34 | gm |
| KOH | 0.65 | gm |

Pichia Feed Medium (for fermentor growth of GS115/pBSAG5)

| | g/L Water | |
|---|---|---|
| $H_3PO_4$(85%) | 3.5 | mL |
| $CaSO_4.2H_2O$ | 0.15 | |
| $K_2SO_4$ | 2.38 | |
| $MgSO_4.7H_2O$ | 1.95 | |
| KOH | 0.65 | |
| $FeSO_4.7H_2O$ | 0.065 | |
| $CuSO_4.5H_2O$ | 0.006 | |
| $ZnSO_4.7H_2O$ | 0.020 | |
| $MnSO_4.H_3O$ | 0.003 | |
| Biotin | 0.000041 | |
| Carbon Source | 20–100 | g |

Trace Salts Solution [for growth of GS115(pBSAGI5I)]

| | g/L Water |
|---|---|
| $CuSO_4.5H_2O$ | 0.06 |
| KI | 0.08 |
| $MnSO_4.H_2O$ | 0.3 |
| $Na_2MoO_4.2H_2O$ | 0.2 |
| $H_3BO_3$ | 0.02 |
| $ZnSO_4.7H_2O$ | 2.0 |
| $FeCl_3.6H_2O$ | 4.8 |
| $H_2SO_4$ | 3–5 mL/L (to remove cloudiness) |
| Ausria dilution buffer | 4.3 mM $Na_2HPO_4$ 1.5 mM $KH_2PO_4$ 2.7 mM KCl 0.15 M NaCl 1% bovine serum albumin 0.02% sodium azide —final pH 7.4 |
| Solubilization buffer | 10 mM Sodium phosphate buffer (pH 7.5) |

-continued

```
0.5 M NaCl
0.1% Triton X-100
2 mM PMSF
```

Unless otherwise specified, the above solutions represent the basic (1x) concentration employed. Throughout the examples, where the difference concentration levels are employed, that fact is indicated by referring to the solution as a multiple of the basic (1x) concentration.

EXAMPLE I

*Pichia pastoris* Transformation Procedure

A. Cell Growth

1. Inoculate a colony of Pichia pastoris GS115 (NRRL Y-15851) into about 10 mL of YPD medium and shake culture at 30° C. for 12-20 hrs.

2. After about 12-20 hrs., dilute cells to an $OD_{600}$ of about 0.01-0.1 and maintain cells in log growth phase in YPD medium at 30° C. for about 6-8 hrs.

3. After about 6-8 hrs, inoculate 100 mL of YPD medium with 0.5 mL of the seed culture at an $OD_{600}$ of about 0.1 (or equivalent amount). Shake at 30° C. for about 12-20 hrs.

4. Harvest culture when $OD_{600}$ is about 0.2-0.3 (after approximately 16-20 hrs) by centrifugation at 1500 g for 5 minutes.

Preparation of Spheroplasts

1. Wash cells once in 10 mL of sterile water. (All centrifugations for steps 1-5 are at 1500 g for 5 minutes.)
2. Wash cells once in 10 mL of freshly prepared SED.
3. Wash cells twice in 10 mL of sterile 1M Sorbitol.
4. Resuspend cells in 10 mL SCE buffer.
5. Add 5-10 µL of 4 mg/mL Zymolyase 60,000 (Miles Laboratories). Incubate cells at 30° C. for about 30-60 minutes.

Since the preparation of spheroplasts is a critical step in the transformation procedure, one should monitor spheroplast formation as follows: add 100 µL aliquots of cells to 900 µL of 5% SDS and 900 µL of 1M sorbitol before or just after the addition of zymolyase and at various times during the incubation period. Stop the incubation at the point where cells lyse in SDS but not in sorbitol (usually between 30 and 60 minutes of incubation).

6. Wash spheroplasts twice in 10 mL of sterile 1M Sorbitol by centrifugation at 1000 g for 5-10 minutes. (The time and speed for centrifugation may vary; centrifuge enough to pellet spheroplasts but not so much that they rupture from the force.)
7. Wash cells once in 10 mL of sterile CaS.
8. Resuspend cells in total of 0.6 mL of CaS.

C. Transformation

1. Add DNA samples (up to 20 µL volume) to 12×75 mm sterile polypropylene tubes. (DNA should be in water or TE buffer; for maximum transformation frequencies with small amounts of DNA, it is advisable to add about 1 µL of 5 mg/mL sonicated *E. coli* DNA to each sample.)
2. Add 100 µL of spheroplasts to each DNA sample and incubate at room temperature for about 20 minutes.
3. Add 1 mL of PEG solution to each sample and incubate at room temperature for about 15 minutes.
4. Centrifuge samples at 1000 g for 5-10 minutes and decant PEG solution.
5. Resuspended samples in 150 µL of SOS and incubate for 30 minutes at room temperature.
6. Add 850 µL of sterile 1M Sorbitol and plate aliquots of samples as described below.

D. Regeneration of Spheroplasts

1. Recipe for Regeneration Agar Medium:
   a. Agar-KCl- 9 g Bacto-agar, 13.4 g KCl, 240 mL H₂O, autoclave.
   b. 10X Glucose- 20 g Dextrose, 100 mL H₂O, autoclave.
   c. 10X SC- 6.75 g Yeast Nitrogen Base without amino acids, 100 mL H₂O, autoclave. (Add any desired amino acid or nucleic acid up to a concentration of 200 µg/mL before or after autoclaving.)
   d. Add 30 mL of 20X glucose and 30 mL of 10X SC to 300 mL of the melted Agar-KCl solution. Add 0.6 mL of 0.2 mg/mL biotin and any other desired amino acid or nucleic acid to a concentration of 20 µg/mL. Hold melted Regeneration Agar at 55-60° C.

2. Plating of Transformation Samples:

Pour bottom agar layer of 20 mL Regeneration Agar per plate at least 30 minutes before transformation samples are ready. Distribute 10 mL aliquots of Regeneration Agar to tubes in a 45°-50° C. bath during the period that transformation samples are in SOS. Add a quantity of each sample to 10 mL aliquots of melted Regeneration Agar held at 45°-50° C. and pour each onto plates containing a solid 10 mL bottom agar layer of Regenation Agar.

3. Determination of Quality of Spheroplast Preparation:

Remove 10 µL of one sample and dilute 100 times by addition to 990 µL of 1M Sorbitol. Remove 10 µL of the 100 fold dilution and dilute an additional 100 times by addition to a second 990 µL aliquot of 1M Sorbitol. Spread plate 100 µL aliquots of both dilutions on YPD agar medium to determine the concentration of unspheroplasted whole cells remaining in the preparation. Add 100 µL of each dilution to 10 mL of Regeneration Agar supplemented with 40 µg/mL histidine to determine total regeneratable spheroplasts. Good values for a transformation experiment are $1-3 \times 10^7$ total regeneratable spheroplasts/mL and about $1 \times 10^3$ whole cells/mL.

4. Incubate plates at 30° C. for 3-5 days.

EXAMPLE II

Construction of the pAOP2 Family of Vectors

1. Plasmid pPG2.5 (a pBR322 based plasmid containing the approximately 2.5 Kbp EcoRI-SalI fragment from plasmid pPG4.0, which plasmid contains the primary alcohol oxidase gene (AOX1) and regulatory regions and which is available in an *E. coli* host from the Northern Regional Research Center of the United States Department of Agriculture in Peoria, Ill. as NRRL B-15868) was digested with BamHI.

2. The linearized plasmid was digested with BAL31;

3. The resulting DNA was treated with Klenow fragment to enhance blunt ends, and ligated to EcoRI linkers;

4. The ligation products were transformed into *E. coli* strain MM294;

5. Transformants were screened by the colony hybridization technique using a synthetic aligonucleotide having the following sequence:

5'TTATTCGAAACGGGAATTCC.

This oligonucleotide contains the AOX1 promoter sequence up to, but not including, the ATG initiation condon, fused to the sequence of the EcoRI linker;

6. Positive clones were sequenced by the Maxam-Gilbert technique. All three positives had the following sequence:

5'... TTATTCGAAACGAGGAATTCC...3'.

They are retained the "A" of the ATG (underlined in the above sequence). It was decided that this A would probably not be detrimental; thus all subsequent clones are derivatives of these positive clones. These clones have been given the laboratory designation pAOP1, pAOP2 and pAOP3, respectively.

7. Two other clones were identified by screening of the BAL31/linker-ligated products. They have the following sequence:

5'...T A A T T A T T C G   G A A T T C C...3'
       pAOX1                 EcoRI

These clones have been designated pAOP5 and pAOP6. In a variation of the above procedure, plasmid pPG2.5 was cut with AsuII, instead of BamHI, the linearized fragment was treated with Klenow fragment (no BAL31 treatment as done above), then ligated to EcoRI linkers. The resulting plasmid contains AOX1 promoter sequences, absent the ATG initiation codon. The plasmid thus prepared has been designed pAOP4, and has the following sequence:

5'...T A A T T A T G   G A A T T C...3'
       pAOX1              EcoRI

The AOX1 promoter (pAOX1) responds to carbon catabolic repression by a severe cessation of enzyme synthesis. In addition, the AO promoter responds to carbon starvation. Growth on methanol leads to a further induction of the AOX1 promoter. Furthermore, it is clear from extensive studies, such as those described by Ellis, Brust, Koutz, Waters, Harpold and Gingeras in Molecular and Cellular Biology, May, 1985, p. 1111–1121, that the AOX1 promoter fragment used in this invention is regulated in a similar fashion to the AOX1 promoter in the chromosome. Each of the clones prepared and isolated as described in this example display responses to catabolic repression, carbon starvation and methanol induction as does the AOX1 promoter itself.

Description of the AO Terminator

The StuI-HindIII fragment used as the AO terminator contains sequences which provide a template for polyadenylation of the AOX1 mRNA transcript. These sequences include the following:

TATAGTATAGGATTTTTTTTGTC-polyadenylation.

When the StuI-HindIII fragment is located on a plasmid 3' to a polypeptide coding region, it promotes RNA termination. The AOX1 termination sequences have been isolated, and can be recovered from plasmid pPG3.2, which is a pBR322-based plasmid containing the AOX1 termination sequences. The plasmid, transformed into an E. coli host, will be available to the public from the Northern Regional Research Center of the United States Department of Agriculture in Peoria, Ill. upon issuance of the application as a patent, under the accession number NRRL B-15999.

EXAMPLE III

Figure 5:
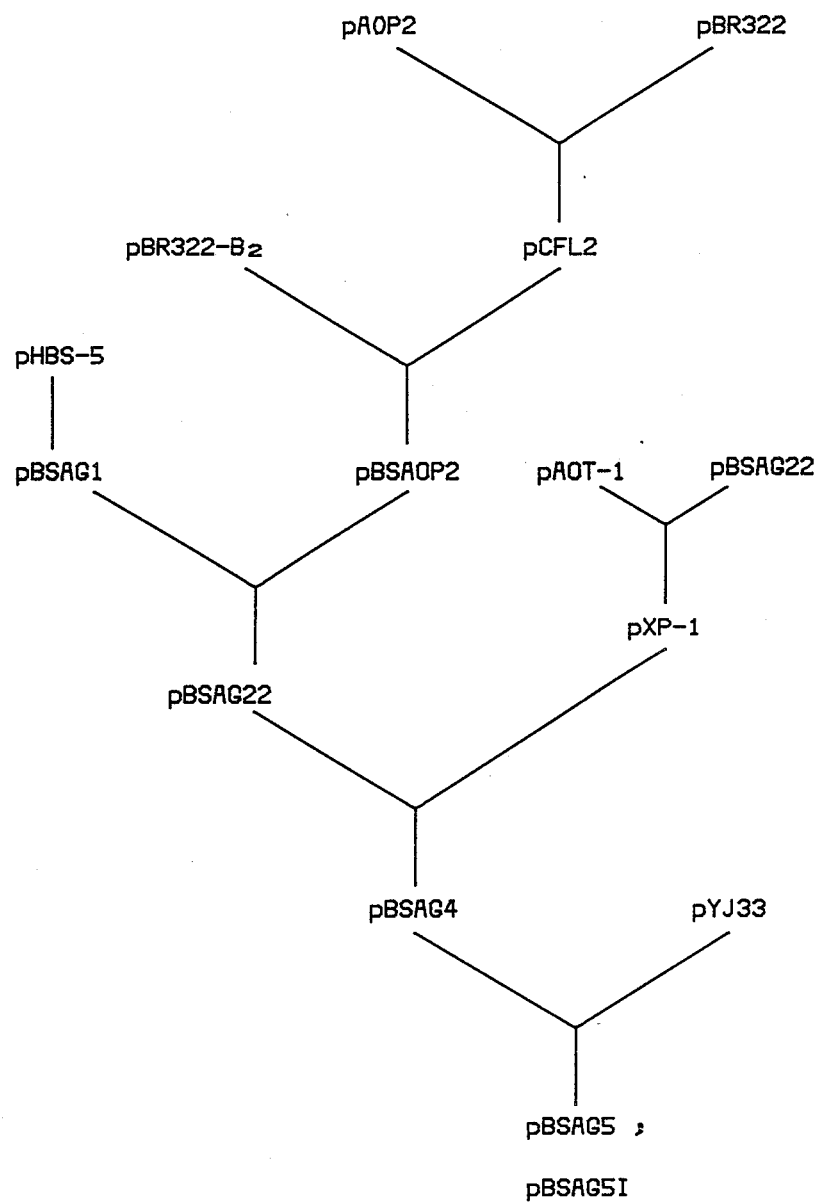
FIG. 5 provides the scheme followed for the construction of plasmids pBSAG5 and pBSAG5.

The sequence of steps employed for the preparation of the plasmids which are the subject of this example are summarized in attached FIG. 5.

Construction of pBSAG5 and pBSAG5I

1. Construction of pCFL2

Vector pAOP2, which contains the AOX1 promoter minus the TG of the ATG at its 3'-end, was cut with HincII. The promoter-containing DNA fragment was isolated and ligated into pBR322 which was previously cut with HindIII and filled in with Klenow fragment. This reaction created vector pCFL2.

2. Construction of pBSAOP2 pBR322-BglII, which is pBR322 with the PvuII site replaced by a BglII site, was digested with EcoRI and ClaI. This linearized plasmid was combined with the 5' AOX1-containing ClaI/EcoRI fragment from pCFL2 in a ligation reaction. The resulting vector was designated pBSAOP2.

3. Construction of pBSAG22

Figure 6:
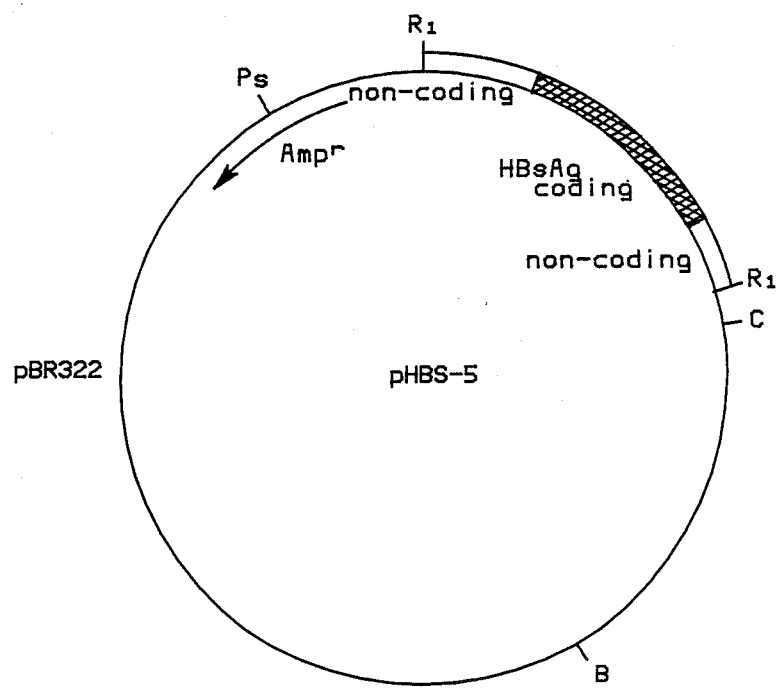
FIG. 6 is a restriction map of plasmid pHBS-5.

Plasmid pHBS-5 (described by Valenzuela et al. in Nature 298, 347–350 (1982); see FIG. 6), which contains the HBsAg gene inserted into the EcoRI site in pBR322, was digested with ClaI. Approximately 60 base pairs were removed in both directions with Bal31 exonuclease. The remaining DNA fragment was digested with BamHI and filled in which Klenow fragment. After ligation, a pool of approximately 200 transformants were cut with NcoI. The linearized plasmids were isolated and religated. After transformation of E. coli, approximately 10% of all plasmids (designated pBSAG1) had a newly created NcoI site. pBSAG1 was digested with NcoI, filled in with Klenow fragment and digested with BamHI. This plasmid fragment was ligated to pBSAOP2, which was previously digested with EcoRI, filled in with Klenow fragment and digested with BamHI. The resulting vector was designated pBSAG22.

4. Construction of pBSAG4, pBSAG5, pBSAG5I

Figure 7:
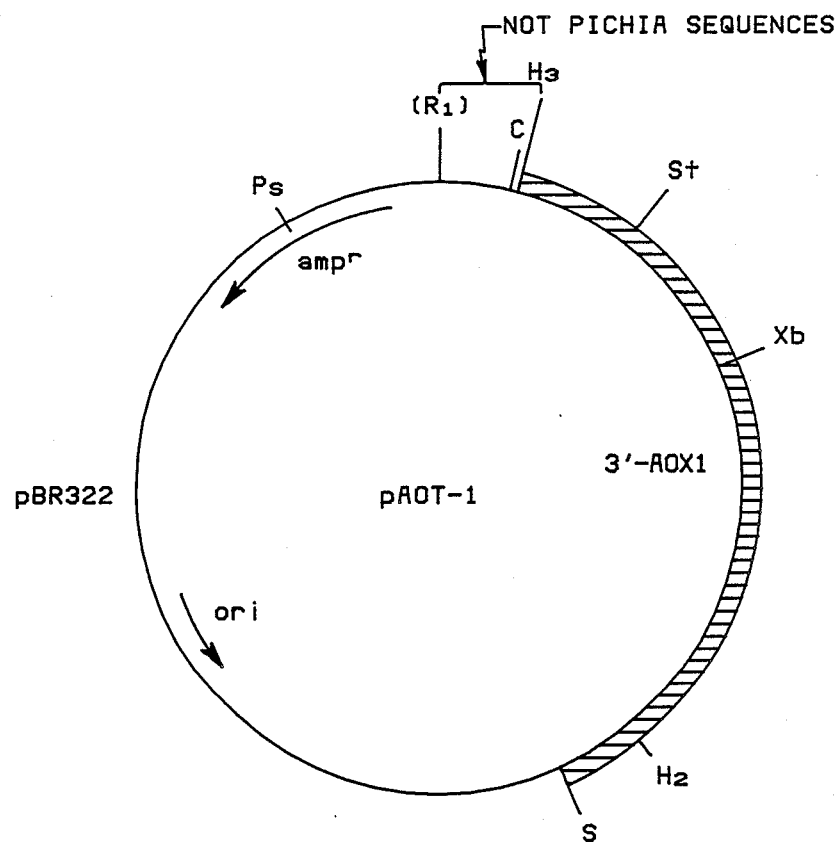
FIG. 7 is a restriction map of plasmid pAOT-1.

Plasmid pAOT-1 (a pBR322 based plasmid derived by ligating, the 1.6 kbp SalI-HindIII fragment of pPG3.2 (available in an E. coli host as NRRL B-15999) into a SalI-HindIII cut pBR322 Δ EcoRI (i.e., pBR322 with the EcoRI site destroyed; see FIG. 7), which carries the 3'-AOX1 transcriptional termination fragment, was cut with XbaI and PstI. The terminator-containing fragment was ligated to pBSAG22, which was previously cut with XbaI and PstI, yielding pXP-1. pBSAG22 was digested with DraI, then StuI linkers were added, and finally StuI and EcoRI were used for further digestion. The HBsAg structural gene was isolated and ligated into pXP-1, which had been previously cut with StuI and EcoRI, yielding pBSAG4.

Figure 8:
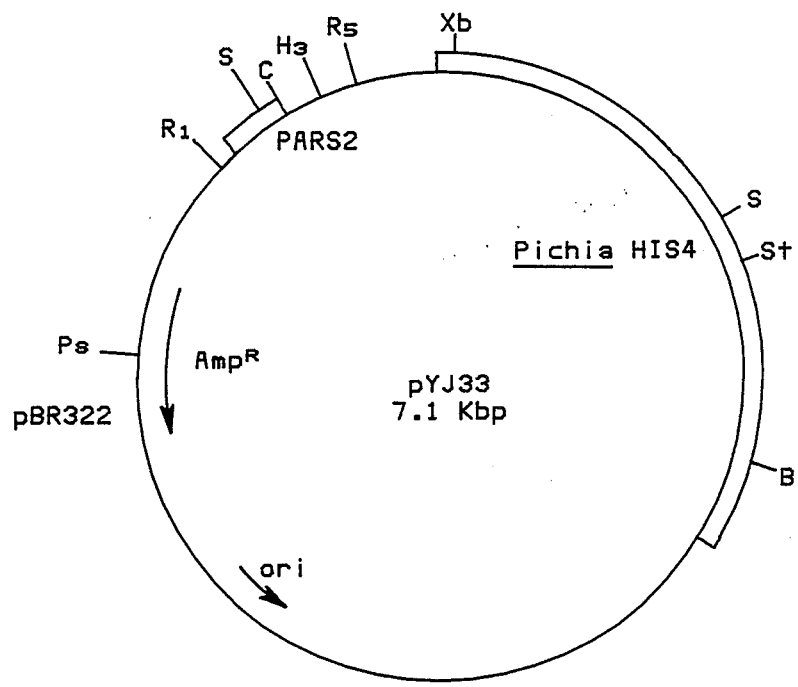
FIG. 8 is a restriction map of plasmid pYJ33.

The HBsAg containing ClaI fragment from pBSAG4 was ligated into the unique ClaI site of pYJ33 (see FIG. 8) yielding pBSAG5 and pBSAG5I. A restriction map of plasmid pBSAG5I is presented in FIG. 11. Plasmids pBSAG5 and pBSAG5I differ only in the orientation of the ClaI fragment which contains the 5'-AOX1/HBsAg/3'-AOX1 expression cassette. Thus, in pBSAG5, the 5'-AOX1 fragment is adjacent to the Pichia HIS4 gene, while the 3'-AOX1 fragment is adjacent to the autonomous element, PARS2. Plasmid pBSAG5, transformed into an *E. coli* host, has been deposited with the Northern Regional Research Center of the United States Department of agriculture to ensure access by the public upon issuance of this application as a patent. The *E. coli* strain MC1061-pBSAG5 has been assigned the accession number NRRL B-18028.

EXAMPLE IV

CONSTRUCTION OF THE PICHIA PASTORIS HBsAg EXPRESSION HOST GS115 (pBSAGI5I)

The preparation of a *Pichia pastoris* host in which the primary alcohol oxidase gene (AOX1) is replaced by the Hepatitis B surface antigen (HBsAg) gene in the Pichia chromosome is described in this Example.

Figure 9:
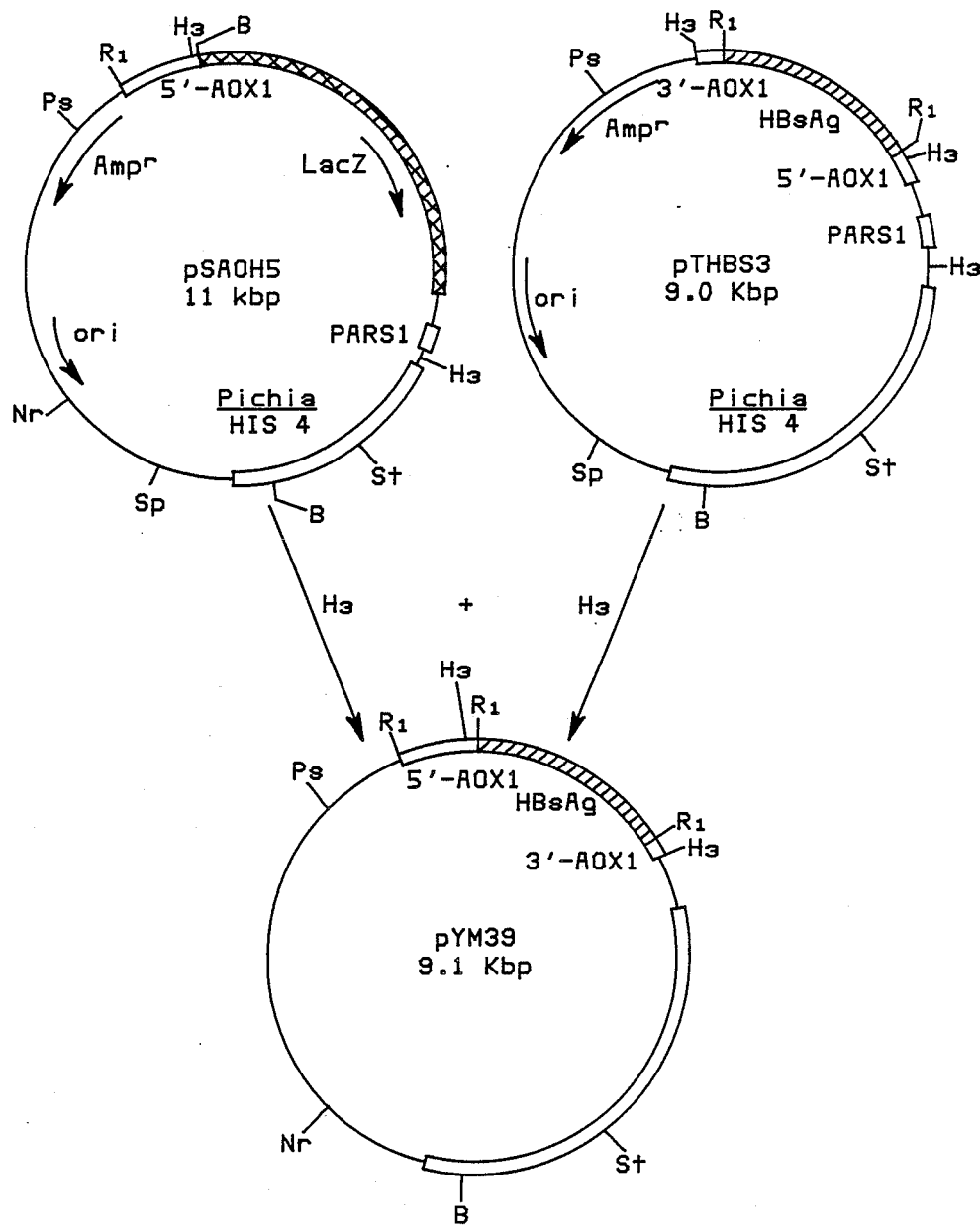
FIG. 9 illustrates the construction of plasmid pYM39 from plasmids pSAOH5 and pTHBS3.
Figure 10:
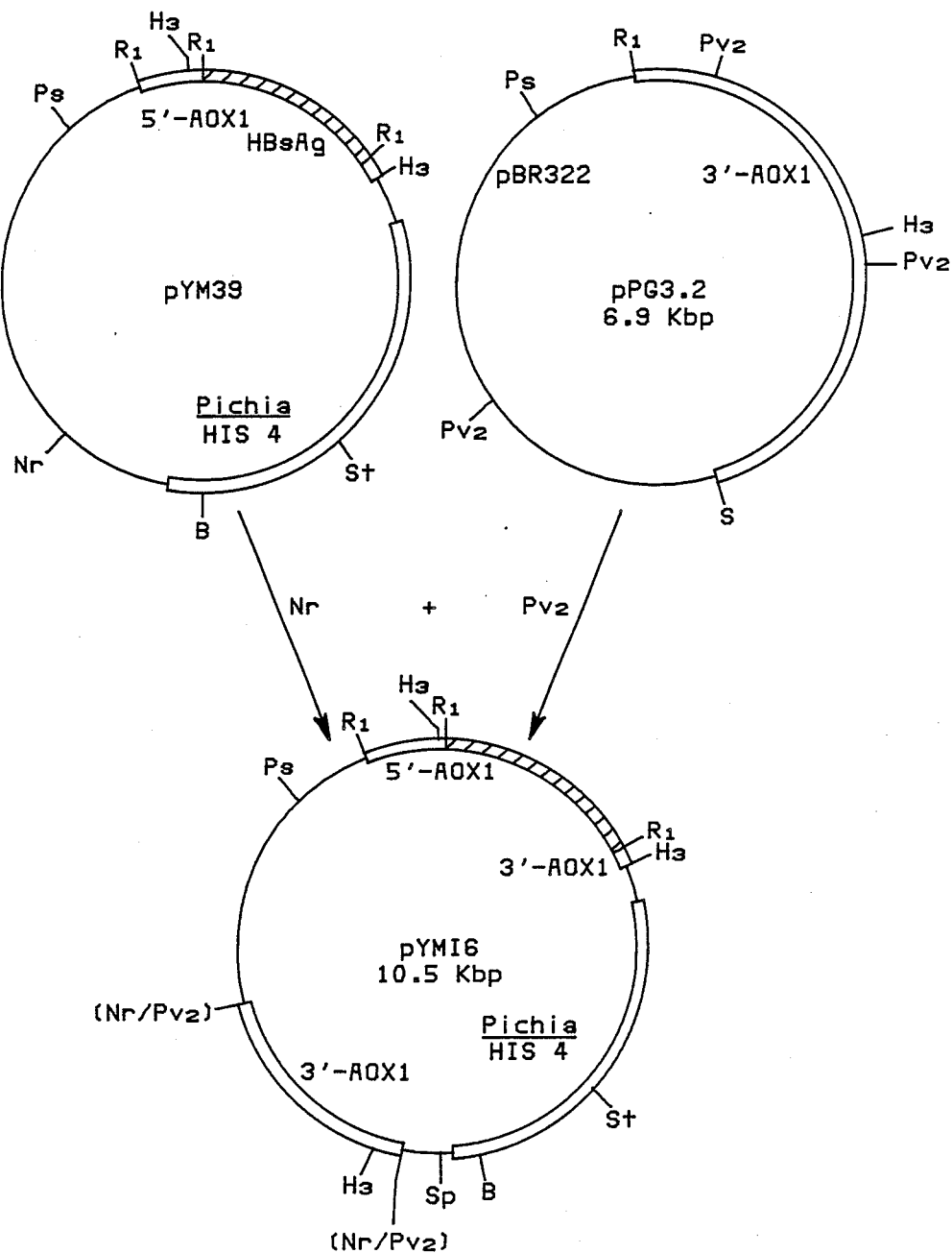
FIG. 10 illustrates the construction of plasmid pYMI6 from plasmids pYM39 and pPG3.2.
Figure 11:
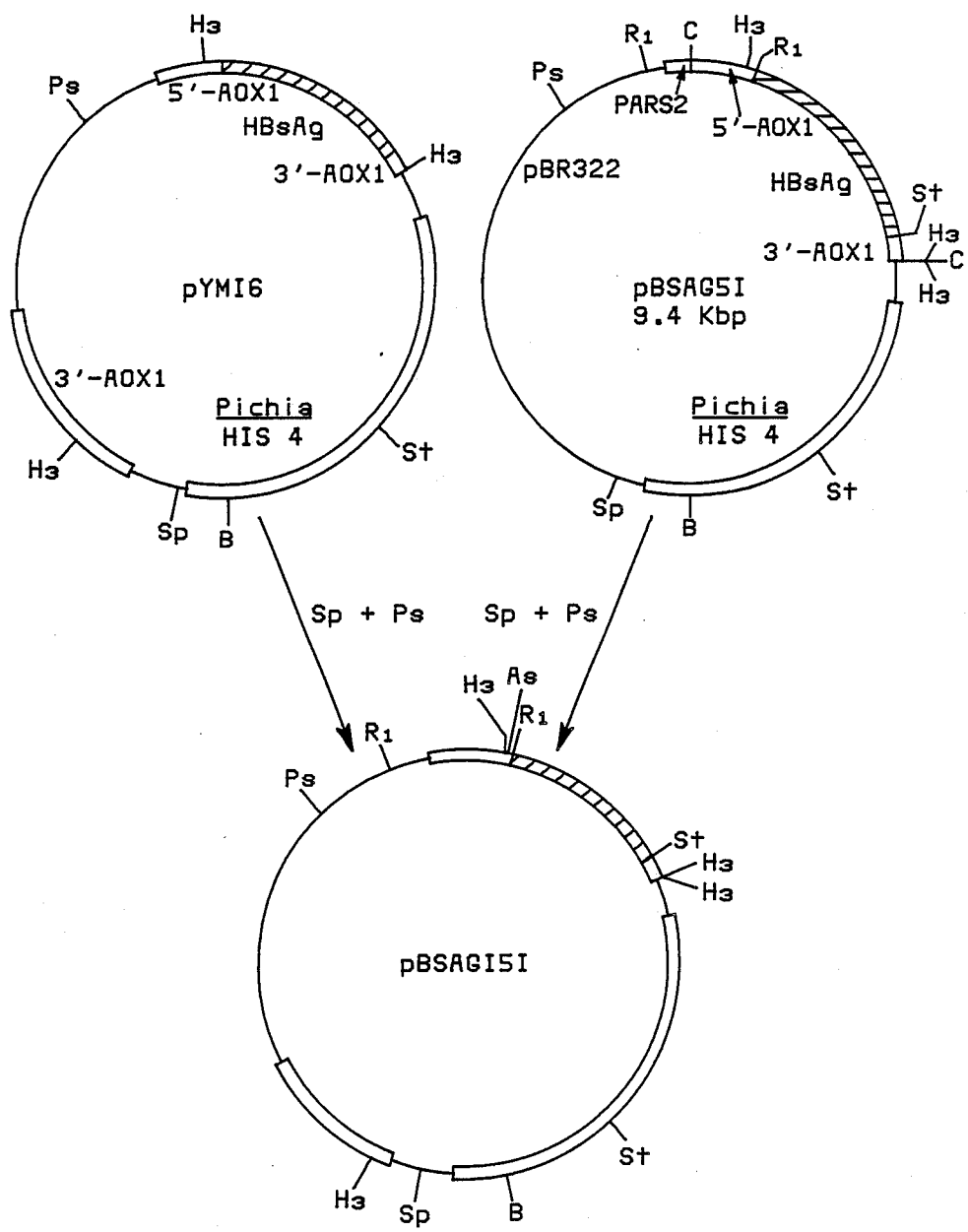
FIG. 11 illustrates the construction of plasmid pBSAGI5I from plasmids pYMI6 and pBSAG5I.
Figure 13:
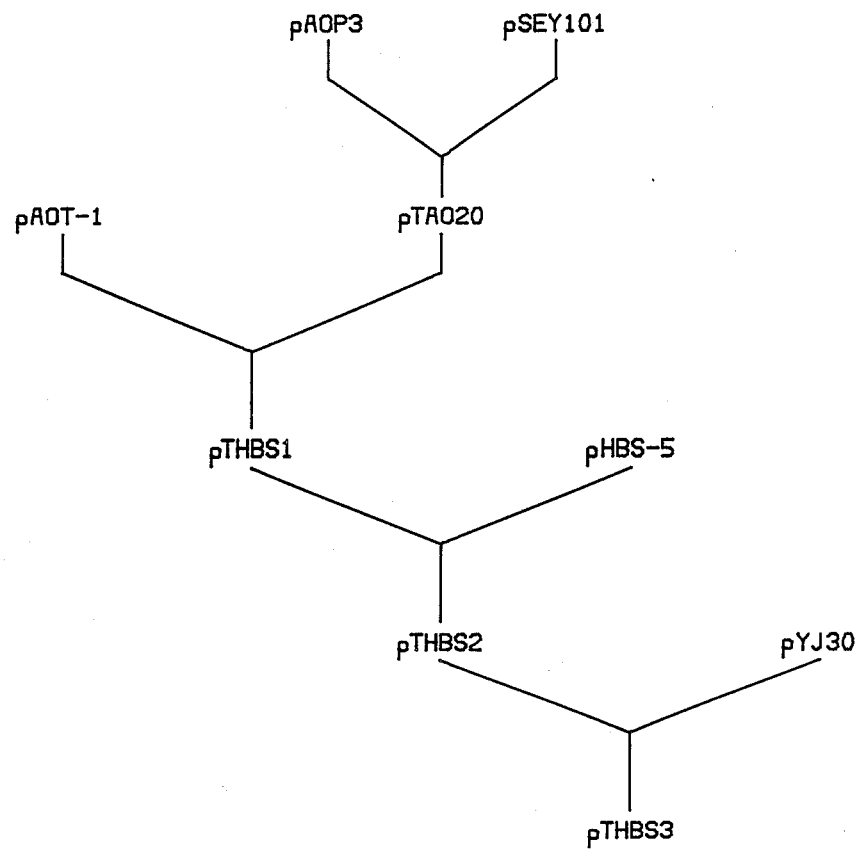
FIG. 13 provides the scheme followed for the construction of plasmid pTHBS3.

To produce the *P. pastoris* HBsAg expression-Aox1⁻ mutant host, plasmid pBSAGI5I was constructed as outlined in FIGS. 9-11. The first step in the construction was to digest the AOX1 promoter-LacZ gene expression vector pSAOH5 and the AOX1 promoter-HBsAg expression vector pTHBS3, prepared as described below and summarized in FIG. 13, with restriction endonuclease HindIII. To prepare pTHBS3, plasmid pAOT-1 (see FIG. 7) was cut with StuI, ligated with EcoRI linkers, and then digested with PstI. The EcoRI- PstI fragment containing the 3'-AOX1 fragment was isolated. Vector pAOP3, which contains 5'-AOX1 sequences, was cut with EcoRI and SstI; the resulting 5'-AOX1 fragment was ligated into the *E. coli-S. cerevisiae* shuttle vector pSEY101 (Douglas et al. (1984) Proc. Natl. Acad. Sci. USA, 81, 3983–3987) which had previously been cut with EcoRI and SstI. The result of ligating these pAOP3 and pSEY101 fragments was plasmid pTAO20. Plasmid pTAO20 contains the URA3 and ampicillin genes for selection in *S. cerevisiae* and bacteria, respectively, the $2\mu$ circle for replication in *S. cerevisiae*, and the 5'-AOX1 sequences.

Plasmid pTAO20 was partially cut with PstI. The linearized vector was isolated and cut with EcoRI. The largest fragment (which contained the $2\mu$ circle sequences, the URA3 gene and the 5'-AOX1 fragment) was ligated to the 3'-AOX1 fragment obtained from pAOT-1, to produce vector pTHBS1.

The HBsAg-containing EcoRI fragment from pHBS-5 was isolated by digestion with EcoRI, then ligated with pTHBS1, which had previously been digested with EcoRI and treated with bacterial alkaline phosphatase. The resulting vector, designated pTHBS2, has the HBsAg gene inserted between the 3'- and 5'-AOX1 sequences.

Plasmid pYJ30 (available in an *E. coli* host as NRRL B-15890) was cut with EcoRI, filled in with Klenow fragment, then cut with PstI. The *P. pastoris* HIS4-/PARS1-containing fragment was isolated and ligated with the PstI-SstI fragment from vector pTHBS2 (which contains the HBsAg gene flanked by the AOX1 sequences). This ligation yields vector pTHBS3.

The 1.4 kbp fragment obtained from pTHBS3 upon digestion with HindIII (which fragment contains the HBsAg gene, the AOX1 termination sequence and a portion of the AOX1 promoter sequence) was recovered and inserted into the 7.7 kbp fragment from pSAOH5, which contains the Pichia HIS4 gene, most of the AOX1 promoter sequence, and sequences from pBR322. A 9.1 kbp recombinant plasmid, pYM39, which contains the restored AOX1 promoter sequences, was then isolated.

For the second construction step, the plasmid pPG3.2 (available in an *E. coli* host as NRRL B-15999) was digested with PvuII and a 1.5 kbp fragment which contains sequences immediately 3' of the AOX1 gene was inserted into the single NruI site of pYM39. A 10.6 kbp recombinant plasmid, pYMI6, was isolated which contained the PvuII fragment oriented such that the 3' AOX1 gene proximal sequences were oriented toward the HIS4 gene portion of the vector. Plasmid pYMI6 contained all components required for deletion of the AOX1 gene from a Pichia host, and expression of HBsAg with AOX1 promoter control, but it does not contain the trimmed HBsAg gene fragment of pBSAG5.

Therefore, the last construction step was to recombine the desired HBsAG gene into an AOX1 gene deletion vector. For this, pYMI6 and pBSAG5I, (a plasmid identical to pBSAG5 except that the ClaI fragment which contains the HBsAg expression cassette is in the opposite orientation) were digested with restriction enzymes PstI and SphI. The 6.3 kbp fragment from pBSAG5I, which contains the trimmed HBsAg gene expression cassette and the Pichia HIS4 gene, was inserted into the 4.6 kbp fragment from pYMI6 which contains the 3' AOX1 sequences and most of pBR322 to produce the final 10.9 kbp plasmid, pBSAGI5I. Plasmid pBSAGI5I, carried in an *E. coli* host, has been deposited with the Northern Regional Research Center in Peoria, Illinois to ensure access by the public upon issuance of this application as a patent, and has been assigned accession number NRRL B-18021.

Figure 12:
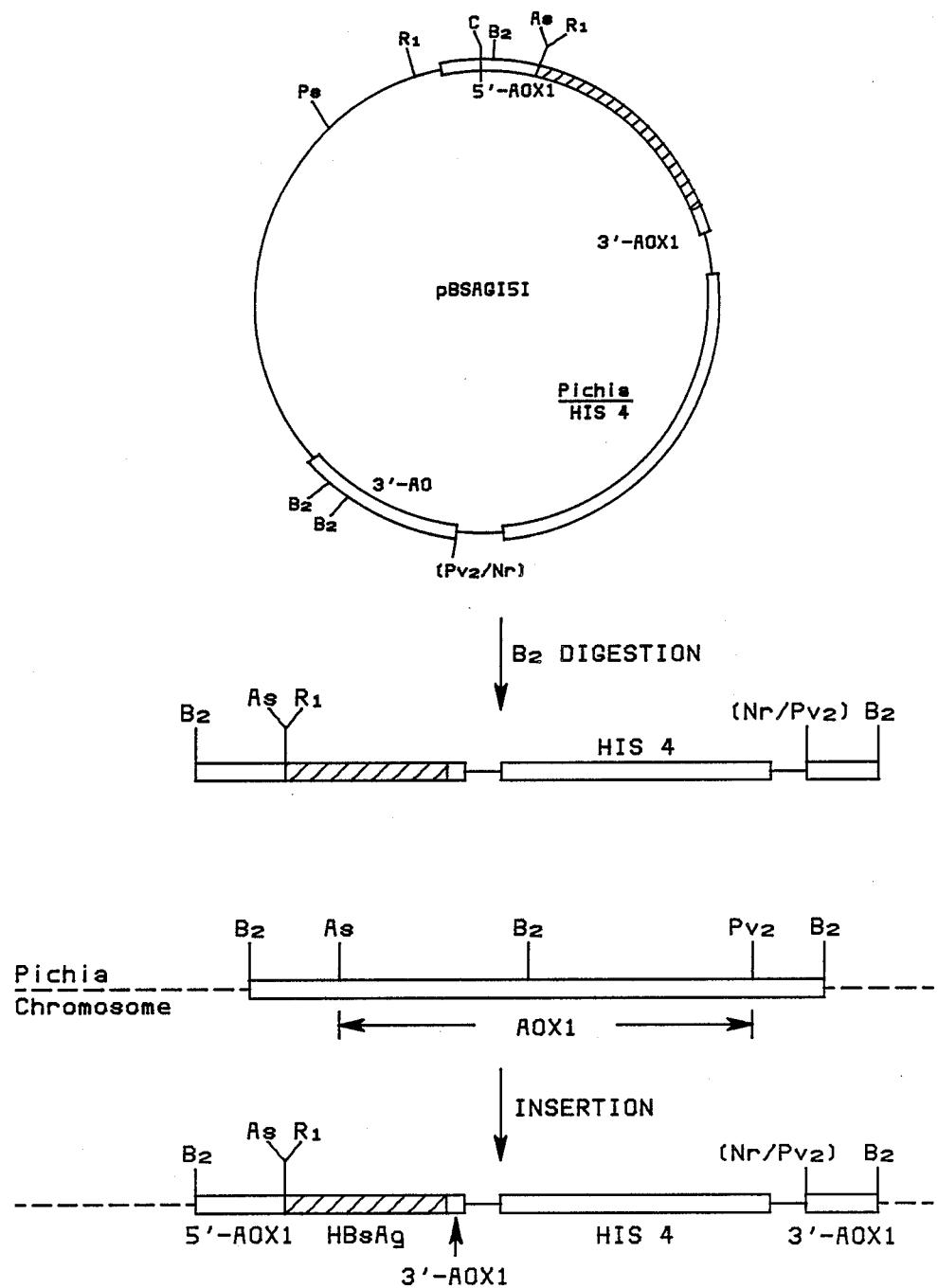
FIG. 12 illustrates the insertion of a portion of plasmid pBSAGI5I into the primary alcohol oxidase (AOX1) locus of the Pichia chromosome.

To transform the *P. pastoris* his4 mutant strain GS115 (NRRL Y-15851), pBSAGI5I was first digested with restriction enzyme BglII to produce a 7.2 kbp linear vector, which contains 0.85 kbp of sequence from 5' of the AOX1 gene at one terminus and 1.1 kbp of sequence from 3' of the AOX1 gene at the other terminus (FIG. 12). About 2 $\mu$g of BglII-cut pBSAGI5I was transformed into GS115 by selection for histidine prototrophy. Approximately $5 \times 10^3$ His+ colonies resulted from the transformation.

Transformation events in which pBSAGI5I was inserted as a linear molecule at the AOX1 chromosomal locus result in the deletion of the AOX1 gene. Therefore, His+-transformed strains in which the desired linear insertion had occurred were identified by their very slow growth rate on methanol. (*P. pastoris* has a second "weaker" alcohol oxidase gene, AOX2, which produces alcohol oxidase sufficient for methanol growth at a slow rate in strains defective in the primary alcohol oxidase gene.)

The procedure for identifying the His+ transformants which could not grow well on methanol was to first recover the His+ cells which were embedded in the selective agar. The recovery step was performed by transferring the agar to a 50 mL tube containing 20 mL of sterile water and pulverizing the agar using a Brinkman homogenizer at low speed for 30 seconds. Agar debris was separated from the cells by filtering the mixture through gauze and rinsing the agar with 30 mL of sterile water. The yeast cells were then diluted to an optical density at $A_{600}$ of 0.1, sonicated for 10 seconds using a Branson sonifier at setting 4 to break apart yeast cell clumps and diluted one hundred fold with sterile water. Aliquots of 10 and 100 $\mu$L were spread on agar plates containing 0.67% yeast nitrogen base without amino acids (Difco) and 0.1% glucose. After incubation at 30° C. for 3 days, colonies which appeared on the plates were screened for the ability to grow on methanol by replica plating the colonies onto a series of agar plates containing 0.67% yeast nitrogen base without amino acids and the following carbon sources: (1) no carbon source; (2) 0.5% methanol; and (3) 2% glucose. Of the colonies which grew on 2% glucose, 32% could not grow well on methanol.

To confirm that the pBSAGI5I sequences were inserted as shown in FIG. 12, total DNA was extracted from one of the *P. pastoris* strains defective in methanol utilization, digested with restriction endonucleases and hybridized by the Southern blot method with $^{32}$P-labelled probes. In one set of Southern blots, DNAs from the Aox1$^-$ strain, GS115 (pBSAGI5I), and the Aox1$^+$ straining GS115, were digested with HingIII and hybridized with labeled pPG4.0, a plasmid composed of the AOX1 gene and sequences from pBR322 available in an *E. coli* host from the Northern Regional Research Center in Peoria, Ill. as NRRL B-15868. A 2.3 kbp fragment which encodes AOX1 was seen in the lanes containing GS115 DNA. However, the 2.3 kbp fragment was absent and no new fragments appeared in lines which contained GB115(pBSAGI5I) DNA. This result demonstrated that the AOX1 gene had been deleted from the GS115(pBSAGI5I) strain.

EXAMPLE V

GROWTH OF PICHIA YEASTS TRANSFORMED WITH HBsAg-ENCODING VECTORS

1. Growth of GS115 (pBSAG5) in a fermentor

A 10% inoculum was grown overnight in yeast nitrogen base (YNB)+2% glucose in a shake flask at 30° C. The inoculum was added to sterilized basal salts (adjusted to pH 4) in the fermentor. Glucose feed was added at a dilution rate of 0.05 to 0.1 h$^{-1}$. When cell density reached a steady state level and fermentor glucose levels approached less than 100 ppm, HBsAg production was induced by changing the feed carbon source to methanol or a 50% glucose-50% methanol mixture.

2. Growth of GS115 (pBSAGI5I) (Aox1$^-$) in a fermentor

Optimum expression of soluble HBsAg Ausria activity (3-4% of soluble protein) has been achieved by growing this Aox1$^-$ organism in a batch mode on glycerol, followed by a methanol-containing feed. Inoculum can be grown on YNB+glycerol. Basal salts plus glycerol (1% and 4% glycerol have been used) and biotin can be autoclaved in the fermentor. After cooling, the pH should be adjusted to be between 3.5 and 5, and trace salts (2.5 mL/L) added before inoculating. One hundred percent methanol can be started before or after the glycerol has been exhausted. Methanol levels as high as 2% do not interfere with HBsAg accumulation, which can continue as for long as 200 hours. However, 5% methanol in the fermentor will stop the accumulation of HBsAg particle.

Growth to higher cell densities has been achieved by increasing the feed salt concentrations. Increased zinc levels are particularly important for increased cell densities when grown on methanol. Higher levels of extractable Ausria activity have been achieved when growth was not limited by zinc, but the extractable protein was also higher, resulting in a net decrease in Ausria activity as a percent of soluble protein.

3. Shake Flask Growth of Cell Cultures of GS115(pBSAG5) and GS115(pBSAGI5I)

A transformed colony was picked and streaked out on a SD plate. A streak of cells was inoculated in 50 mL of YNB broth (1×YNB, 5 μg/mL of biotin) with 5% glucose in a 250 mL shake flask, and shaken at 30° C. at 250 revolutions per minute in an airshaker overnight. The morning OD$_{600}$ reading was between 2-3. 100 OD$_{600}$ units of cells (about 10$^9$ cells) were removed from the shake flask and centrifuged in an IEC centrifuge for 7 minute at 2000 Xg at room temperature. The cell pellet was resuspended in 500 mL YNB broth with 2% glycerol in a 2 liter shake flask (OD$_{600}$=0.2). The culture was incubated at 30° C. and 250 rpm in an airshaker until the OD$_{600}$ reached 2 to 3 OD$_{600}$. In the case of the Aox1$^-$ host, 500 OD$_{600}$ were removed from the culture. The cell suspension was centrifuged in an IEC for 7 minutes at 2000 Xg. The cell pellet was resuspended in 500 mL YNB broth with 0.5% methanol (1.0 OD$_{600}$). In the case of the Aox1$^+$ host, 170 OD$_{600}$ of cells were removed from the culture, centrifuged under the same conditions and resuspended in 500 mL YNB broth with 0.5% methanol (0.3 OD$_{600}$). Both cultures were shaken in 2 liter shake flasks at 30° C. and 250 rpm. Whenever an OD$_{600}$≧2 was obtained, the cultures were diluted two-fold with the same growth media. 100 OD$_{600}$ samples were removed periodically and centrifuged for 7 min at 2000 Xg. The resulting cell pellets can be stored frozen at −70° C. for 1 to 2 weeks.

EXAMPLE VI

ASSAYS OF HBsAg: 22 nm PARTICLE AND HBsAg MONOMER

1. Preparation of Extracts and Protein Determination

All of the following operations were performed at 0°-4° C. The frozen cell pellet was thawed, then washed twice with 2 mL of ice cold Solubilization buffer. The cells (100 OD$_{600}$ units) were transferred into a disposable glass tube (13×100 mm). 0.35 mL of Solubilization buffer and 0.5 g of acid-washed glass beads (0.45 mm in diameter) were added to the cell pellet. This suspension was shaken on a vortex mixer on maximum setting 4 times for 1 minute each, and held for 1 minute intervals between each shaking on ice. The whole cell slurry was removed and the glass beads were washed with 0.35 mL Solubilization buffer. The wash buffer was combined with the cell slurry and transferred into an Eppendorf tube. The extract was centrifuged in an Eppendorf centrifuge for 15 minutes. The supernatant (soluble fraction; 0.7 mL) was removed from the pellet. To extract HBsAg protein from the pellet, 0.7 mL of 2× concentrated SDS-gel loading buffer was added to the pellet, and the mixture was stirred on a vortex mixer and boiled for 15 minutes. The mixture was centrifuged for 15 minutes, then the supernatant (insoluble fraction) was removed from the cell debris. Aliquots from the soluble and insoluble fractions were assayed for protein content using the TCA precipitation and the Lowry method. BSA served as a protein concentration standard. Both the insoluble and soluble fractions usually had protein concentrations in the range of 3-15 mg/mL.

2. Alternate Procedure for Preparation of Extracts

This protocol describes conditions for extraction of the monomeric heterologous protein HBsAg, or the protein complex, 22 nm particle, from cultures of *Pichia* pastoris transformed with vectors containing sequences that code for the HBsAg protein.

Cultures of P. pastoris were grown to a cell density of 10–100 OD$_{600}$ units per milliliter. An aliquot of 100 OD$_{600}$ units was transferred to a 13×100 mm borosilicate culture tube and washed twice with 20 volumes of solubilization buffer.

The cells were pelleted, then to the pelleted cells (IEC clinical centrifuge) was added 0.5 g of acid-washed glass beads (0.5 mm) followed by 0.35 mL of solubilization buffer. The solubilization buffer contained either 0.5M NaCl and 0.1% Triton X-100 (wt/vol.) as a control, or a 3M concentration of potassium iodide or potassium thiocyanate, in the presence or absence of 0.1% Triton X-100. All solutions were buffered at pH=7.5 with 10 mM sodium phosphate. The mixture was agitated for four, one-minute intervals at maximum speed using a vortex mixer. Between intervals the mixture was cooled on ice for not less than one minute. After lysing was completed. the solution of broken cells was removed, the glass beads were washed with 0.35 mL of solubilization buffer, and the two solutions were combined and subjected to centrifugation for 15 minutes at 13,000 xg. The supernatants were removed and assayed for immunoreactive HBsAg particle (Ausria assay) and total trichloroacetic acid precipitable protein (Lowry). The results, as a range of 5 experiments, are presented in Table I.

TABLE I

| Lysing Conditions | A HBsAg 22 nm Particle (μg/mL) | B Total Protein (μL/mL) | C HBsAg 22 nm Particle/Protein (wt %) |
| --- | --- | --- | --- |
| Salt (conc.) | | | |
| NaCl (0.5 M) + Triton | 203–249 | 8.6–11.2 | 2.1–3.2 |
| KI (3M) + Triton | 5.1–150 | 0.85–3.4 | 0.5–8.1 |
| KI (3M) − Triton | 71–136 | 2.5–4.3 | 2.3–7.2 |
| KSCN (3M) + Triton | 2.4–50 | 0.6–1.9 | 0.8–9.6 |
| KSCN (3M) − Triton | 80–125 | 1.6–4.3 | 3.8–16.7 |

While none of the conditions containing potassium iodide or potassium thiocyanate, yields values for HBsAg particle higher than the conditions employing sodium chloride (column A), it is clear that potassium iodide or potassium thiocyanate, inhibit the release of total protein (column B), thereby increasing the specific activity of the particle 2–5 fold (column C).

3. 22 nm Particle Assays (AUSRIA™ II kit)

The soluble fraction was diluted 1000 to 10,000-fold with Ausria dilution buffer, and aliquots between 25 and 100 μL were assayed as follows:

First Incubation

1. To construct a standard curve, a dilution series containing between 0.1 ng up to 4 ng of control in a total volume of 200 μL each was pipetted into the bottom of individual wells of a reaction tray (along with 4 negative controls).

For the samples to be analyzed, 200 μL of each diluted soluble fraction was pipetted into the bottom of separate wells of the reaction tray.

2. One bead was carefully added to each well containing a sample fraction or control. Alternatively, beads may be dispensed prior to the addition of controls or samples.

3. The cover seal was applied to the reaction tray, which was then gently tapped to cover the beads and to remove any trapped air bubbles.

4. The reaction was then incubated at 45° C. for 2 hours.

5. The cover seal was removed and discarded. The liquid was aspirated, and each bead washed two times with 4 to 6 mL of distilled or deionized water.

Second Incubation 6. 200 μL of $^{125}$I-Anti-HBs was pipetted into each well containing a bead.

7. A new cover seal was applied, and the reaction tray gently tapped to cover the beads and to remove any trapped air bubbles.

8. The reaction tray was then incubated at 45° C. for 1 hour.

9. The cover seal was removed and discarded. The liquid was aspirated and each bead washed four times as in step 5.

10. The beads were then immediately transferred to properly identified counting tubes.

Gamma Scintillation Counter Reading:

11. The count rate was determined for one minute.

12. The samples were counted within 24 hours after the final wash.

The level of 22 nm particles was calculated using the standard curve generated as described in step 1.

4. Monomer Assay (Western Assay)

The equivalent volume of 25 μg of protein (soluble or insoluble fraction), usually 2–5 μL, was brought up with H$_2$O to 10 μL. 10 μL of 2× concentrated SDS gel loading buffer (100 mM DTT in 1× buffer) was added and the sample was boiled for 15 min. The boiled samples were loaded on a 12% SDS acrylamide gel (Laemmli). After gel electrophoresis, the proteins were transferred to nitrocellulose paper (Towbin et al. Proc. Natl. Acad. Sci. USA 76, 4350–4354 (1979)). The HBsAg was detected with HBsAg antisera (raised against plasma-derived HBsAg) and $^{125}$I-labelled protein A. The nitrocellulose paper was exposed to Kodak XAR-5 film overnight at −70° C. Quantitation of monomer was done by counting the radioactive bands from the nitrocellulose paper in a gamma-counter. Recombinant HBsAg produced by S. cerevisiae (100–500 ng/lane) was used as a standard.

EXAMPLE VII

Expression Levels of HBsAg in Pichia pastoris

The production of HBsAg by several transformed P. pastoris strains was determined by the assay protocol set forth in Example VI, using the solubilization protocol described in part 1 of Example VI. Results are summarized in Table II.

TABLE II

| transformed strain | GS115 (pBSAGI5I) | GS115 (pBSAG5) |
| --- | --- | --- |
| phenotype | Aoxl$^-$ His$^+$ | Aoxl$^+$ His$^+$ |
| state of vector | integrated | autonomous |
| HBsAg level$^a$ (shake flask) | | |
| cells/L | 10$^{11}$ | 10$^{11}$ |
| monomer (%) | 7 | 1.5 |
| 22 nm particle (%) | 2.5 | 0.2 |
| monomer (mg/L)$^b$ | 8.4 | 1.8 |
| 22 nm particle (mg/L)$^b$ | 3 | 0.24 |

TABLE II-continued

| transformed strain | GS115 (pBSAGI5I) | GS115 (pBSAG5) |
|---|---|---|
| HBsAg level[a] (fermentor growth) | | |
| cells/1 | $3.5 \times 10^{12}$ | $8 \times 10^{12}$ |
| monomer (%) | 7 | 1 |
| 22 nm particle (%) | 2.9 | 0.1 |
| monomer (mg/L)[b] | 294 | 96 |
| 22 nm particle (mg/L)[b] | 122 | 10 |

[a]protein assays; measured by the Bradford Method
[b]HBsAg per liter of culture medium; $OD_{600} = 5 \times 10^7$ cells/mL = 0.14 mg dry weight/mL = 0.06 mg protein/mL The results presented above demonstrate that high levels of HBsAg can be produced in *Pichia pastoris* when under control of the primary alcohol oxidase gene (AOX1) regulatory region from *Pichia pastoris*.

The examples have been provided merely to illustrate the practice of the invention and should not be read so as to limit the scope of the invention or the appended claims in any way. Reasonable variations and modifications, not departing from the essence and spirit of the invention, are contemplated to be within the scope of patent protection desired and sought.

What is claimed is:

1. An essentially pure culture of a yeast capable of growth on methanol as carbon and energy source wherein said yeast is of the genus Pichia transformed with an expression cassette comprising
   (a) a regulatory region isolated from *Pichia pastoris* and selected from the group consisting of AOX1, p40, and DAS operably linked to
   (b) a polypeptide coding region coding for a hepatitis B surface antigen operably linked to
   (c) a Pichia transcription termination fragment.

2. An essentially pure culture of a strain of a strain of *Pichia pastoris* capable of growth on methanol as a carbon and energy source transformed with a plasmid selected from the group consisting of:
   pBSAG5,
   pBSAG5I, and
   pBSAGI5I.

3. An isolated DNA fragment comprising:
   (a) a regulatory region isolated from *Pichia pastoris* and selected from the group consisting of AOX1, p40 and DAS, said regulatory region being capable of controlling the transcription of messenger RNA when positioned at the 5' end of the polypeptide encoding region; wherein said regulatory region is responsive to the presence of methanol in the culture medium with which a host organism containing said DNA fragment is in contact; and
   (b) a polypeptide coding region operably linked to said regulatory region and coding for heptatitis B surface antigen.

4. A DNA fragment in accordance with claim 3 wherein said regulatory regions characterized as shown by the restriction map in FIG. 2 of the drawings.

5. A DNA fragment in accordance with claim 3 further comprising a 3' sequence of DNA downstream of the polypeptide coding region; wherein said 3' sequence of DNA is capable of controlling the polyadenylation and termination of transcription of messenger RNA coded for by said polypeptide coding region.

6. A DNA fragment in accordance with claim 3 wherein said DNA fragment further comprises one or more additional DNA sequences selected from the group consisting of
   bacterial plasmid DNA,
   bacteriophage DNA,
   yeast plasmid DNA, and
   yeast chromosomal DNA.

7. A DNA fragment in accordance with claim 6 wherein said yeast chromosal DNA comprises an autonomously replicating DNA sequence and a marker gene.

8. A DNA fragment in accordance with claim 3 wherein said DNA fragment further comprises one or more additional DNA sequences selected from the group consisting of
   bacterial plasmid DNA,
   bacteriophage DNA,
   yeast plasmid DNA, and
   yeast chromosomal DNA.

9. A DNA fragment is accordance with claim 8 wherein said yeast chromosomal DNA comprises an autonomously replicating DNA sequence and a marker gene.

10. A DNA fragment in accordance with claim 3 further comprising serially arranged DNA which comprises:
    a first insertable DNA fragment,
    a selectable marker gene, and
    a second insertable DNA fragment;
    wherein said first and second insertable DNA fragments are each at least about 200 nucleotides in length and have nucleotide sequences which are homologous with portions of the genomic DNA of species of the genus Pichia; wherein said DNA fragment and said marker gene are positioned between the 3' end of said first insertable DNA fragment and the 5' end of said second insertable DNA fragment; and wherein said first and second insertable DNA fragments are oriented with respect to one another as they are so oriented in the genome of Pichia.

11. A DNA fragment in accordance with claim 3 wherein said polypeptide coding region consists essentially of the approximately 700 base pair EcoRI-StuI fragment depicted below:

| | | | |
|---|---|---|---|
| 5'-GAATTCATGG | AGAACATCAC | ATCAGGATTC | CTAGGACCCC |
| TGCTCGTGTT | ACAGGCGGGG | TTTTTCTTGT | TGACAAGAAT |
| CCTCACAATA | CCGCAGAGTC | TAGACTCGTG | GTGGACTTCT |
| CTCAATTTTC | TAGGGGGATC | TCCCGTGTGT | CTTGGCCAAA |
| ATTCGCAGTC | CCCAACCTCC | AATCACTCAC | CAACCTCCTG |
| TCCTCCAATT | TGTCCTGGTT | ATCGCTGGAT | GTGTCTGCGG |
| CGTTTTATCA | TATTCCTCTT | CATCCTGCTG | CTATGCCTCA |
| TCTTCTTATT | GGTTCTTCTG | GATTATCAAG | GTATGTTGCC |
| CGTTTGTCCT | CTAATTCCAG | GATCAACAAC | AACCAGTACG |
| GGACCATGCA | AAACCTGCAC | GACTCCTGCT | CAAGGCAACT |
| CTATGTTTCC | CTCATGTTGC | TGTACAAAAC | CTACGGATGG |
| AAATTGCACC | TGTATTCCCA | TCCCATCGTC | CTGGGCTTTC |
| GCAAAATACC | TATGGGAGTG | GGCCTCAGTC | CGTTTCTCTT |

-continued

| | | | |
|---|---|---|---|
| GGCTCAGTTT | ACTAGTGCCA | TTTGTTCAGT | GGTTCGTAGG |
| GCTTTCCCCC | ACTGTTTGGC | TTTCAGCTAT | ATGGATGATG |
| TGGTATTGGG | GGCCAAGTCT | GTACAGCATC | GTGAGTCCCT |
| TTATACCGCT | GTTACCAATT | TTCTTTTGTC | TCTGGGTATA |
| CATTTAAGGC | CT-3' | | |

12. A plasmid comprising:
the DNA fragment of claim 3,
bacterial plasmid DNA,
a selectable yeast marker gene, and
a yeast autonomous replication sequence.

13. A plasmid in accordance with claim 12 wherein said plasmid is pBSAG5.

14. A plasmid in accordance with claim 12 wherein said plasmid is pBSAG5I, as depicted in FIG. 11.

15. A plasmid in accordance with claim 12 wherein said plasmid is pBSAGI5I, as depicted in FIG. 11.

16. An essentially pure culture of a strain of the *Pichia pastoris* transformed with the DNA fragment of claim 5.

17. A process for preparing hepatitis B surface antigen which comprises cultivating *Pichia pastoris* transformed with the plasmid of claim 12 in a nutrient medium which comprises methanol.

18. A process in accordance with claim 17 further comprising isolating and purifying said hepatitis B surface antigen.

19. A DNA fragment in accordance with claim 3 wherein said regulatory region is characterized as shown by the restriction map in FIG. 1(b) of the drawings.

20. A DNA fragment in accordance with claim 3 wherein said regulatory region is characterized as shown by the restriction map in FIG. 3 of the drawings.

21. A process for the production of hepatitis B surface antigen comprising:
(a) transforming *Pichia pastoris* capable of growth on methanol as a carbon and energy source with an expression cassette containing a polypeptide coding region for a hepatitis B surface antigen operably linked to a regulatory region derived from *Pichia pastoris* and selected from the group consisting of AOX1, p40 and DAS and a transcription termination fragment; and thereafter
(b) culturing the resulting transformed *Pichia pastoris* on methanol as a carbon and energy source under suitable conditions to obtain the production of hepatitis B surface antigen.

22. The process of claim 21 wherein said expression cassette is contained within a vector which is selected from the group consisting of circular or linear plasmids.

23. The process of claim 22 wherein the plasmid is linear.

24. The process of claim 23 wherein the linear plasmid is a site directed integration vector.

25. The process of claim 24 wherein said site directed integration vector contains the following serial arrangement:
(a) a first insertable DNA fragment,
(b) a marker gene, and expression cassette containing a polypeptide coding region coding for a hepatitis B surface antigen operably linked to a regulatory region and a transcription termination fragment, and
(c) a second insertable DNA fragment;
wherein the marker gene and cassette of component (b) are positioned between the 3' end of the first insertable DNA fragment and the 5' end of the second insertable DNA fragment.

26. The process of claim 25 wherein the first insertable DNA fragment and the second insertable DNA fragment are derived from the DNA sequence of a gene isolated from *Pichia pastoris*.

27. The process of claim 25 wherein said marker gene is isolated from *Pichia pastoris*.

28. The process of claim 25 wherein the transformed *Pichia pastoris* capable of growth on methanol as a carbon and energy source is *Pichia pastoris* GS115.

29. The process of claim 25 wherein the transformed *Pichia pastoris* capable of growth on methanol as a carbon and energy source is *Pichia pastoris* GS190.

30. The process of claim 25 wherein the transformed *Pichia pastoris* is *Pichia pastoris* PPF1.

31. The process of claim 25 wherein said vector comprises
(a) a first insertable DNA fragment which is about one kilobase of the 5' AOX1 regulatory region isolated from *Pichia pastoris* operably linked to
(b) a hepatitis B surface antigen gene operably linked to
(c) the transcription termination fragment of AOX1 isolated from *Pichia pastoris* ligated to
(d) a marker gene which is HIS4 isolated from *Pichia pastoris* ligated to
(e) a second insertable DNA fragment which is about 0.65 kilobases of the AOX1 transcription termination fragment.

* * * * *